US011246608B2

(12) United States Patent
Won (10) Patent No.: US 11,246,608 B2
(45) Date of Patent: Feb. 15, 2022

(54) DEVICE FOR FIXING SPINE

(71) Applicant: Yougun Won, Daejeon (KR)

(72) Inventor: Yougun Won, Daejeon (KR)

( * ) Notice: Subject to any disclaimer, the term of this patent is extended or adjusted under 35 U.S.C. 154(b) by 250 days.

(21) Appl. No.: 16/476,405

(22) PCT Filed: Aug. 25, 2017

(86) PCT No.: PCT/US2017/048611
§ 371 (c)(1),
(2) Date: Jul. 8, 2019

(87) PCT Pub. No.: WO2018/128647
PCT Pub. Date: Jul. 12, 2018

(65) Prior Publication Data
US 2020/0046382 A1 Feb. 13, 2020

(51) Int. Cl.
*A61B 17/17* (2006.01)
*A61L 31/02* (2006.01)
(Continued)

(52) U.S. Cl.
CPC ........ *A61B 17/1757* (2013.01); *A61L 31/022* (2013.01); *A61L 31/06* (2013.01);
(Continued)

(58) Field of Classification Search
CPC .................................................. A61B 17/1757
See application file for complete search history.

(56) References Cited

U.S. PATENT DOCUMENTS 6,338,734 B1 * 1/2002 Burke .................... A61B 17/74
606/280
7,416,553 B2 8/2008 Patel et al.
(Continued)

FOREIGN PATENT DOCUMENTS

KR   10-2007-0048119   5/2007
KR   10-2008-0059920   7/2008
(Continued)

OTHER PUBLICATIONS

International Search Report for International Application No. PCT/US2017/048611, dated Dec. 29, 2017.
(Continued)

*Primary Examiner* — Christian A Sevilla
(74) *Attorney, Agent, or Firm* — Novick, Kim & Lee, PLLC; Jae Youn Kim; Jihun Kim (57) ABSTRACT

A patient-specific drill template for spine screw placement includes a hook-shaped main body, and an insertion guiding portion that guides a spine screw to be inserted into a vertebra. The main body includes a tight contact portion and a hook portion, the tight contact portion connecting with insertion guiding portion, the hook portion extending from the tight contact portion, and the main body partially surrounds the vertebra. A method of preparing a patient-specific drill template for spine screw placement includes preparing a three-dimensional computed tomography of a lumbar or thoracic spine in a hospital; transferring the CT data to the manufacturing facility using a network; processing the computed tomography to generate a three-dimensional reconstruction template of the patient-specific drill template in the facility; preparing the patient-specific drill template based on the reconstruction template; packaging the template and sterilizing the patient-specific drill template.

29 Claims, 6 Drawing Sheets

(51) Int. Cl.
 *A61L 31/06* (2006.01)
 *A61B 17/70* (2006.01)
 *A61B 17/00* (2006.01)
 *A61B 17/56* (2006.01)

(52) U.S. Cl.
 CPC . *A61B 17/7076* (2013.01); *A61B 2017/00526* (2013.01); *A61B 2017/564* (2013.01); *A61B 2017/568* (2013.01)

(56) References Cited

U.S. PATENT DOCUMENTS

| | | | |
|---|---|---|---|
| 7,981,117 | B2 | 7/2011 | Newton et al. |
| 2001/0037111 | A1* | 11/2001 | Dixon ................ A61B 17/7007 606/261 |
| 2004/0230202 | A1 | 11/2004 | Tromanhauser et al. |
| 2007/0179493 | A1* | 8/2007 | Kim .................. A61B 17/7062 606/33 |
| 2008/0287954 | A1* | 11/2008 | Kunz .................. A61B 17/175 606/87 |
| 2010/0152784 | A1* | 6/2010 | Lowry ............... A61B 17/7059 606/282 |
| 2010/0152793 | A1* | 6/2010 | Lowry .................. A61B 17/88 606/86 R |
| 2011/0238181 | A1* | 9/2011 | Trieu ................. A61B 17/1735 623/17.11 |
| 2013/0053854 | A1* | 2/2013 | Schoenefeld ......... A61B 90/92 606/87 |
| 2013/0123850 | A1* | 5/2013 | Schoenefeld ...... A61B 17/7055 606/248 |
| 2013/0145812 | A1* | 6/2013 | Kawaguchi ............... B21F 1/00 72/372 |
| 2014/0163564 | A1* | 6/2014 | Bollinger ........... A61B 17/1666 606/91 |
| 2014/0172025 | A1* | 6/2014 | Vaughan ........... A61B 17/1757 606/309 |
| 2015/0335371 | A1 | 11/2015 | Ono et al. |
| 2015/0374412 | A1* | 12/2015 | Walsh ................ A61B 17/7062 606/249 |
| 2016/0030067 | A1* | 2/2016 | Frey ....................... A61B 17/15 606/86 A |
| 2016/0270802 | A1 | 9/2016 | Fang et al. |
| 2018/0185065 | A1* | 7/2018 | McNally ............ A61F 2/30942 |

FOREIGN PATENT DOCUMENTS

| | | | | |
|---|---|---|---|---|
| KR | 10-0974498 | | 8/2010 | |
| KR | 10-2015-0067809 | | 6/2015 | |
| WO | 2015/187397 | | 12/2015 | |
| WO | WO-2015187397 | A1 * | 12/2015 | ............. G09B 23/30 |
| WO | 2016/019424 | | 2/2016 | |
| WO | WO-2017001851 | A1 * | 1/2017 | ............. A61B 34/10 |

OTHER PUBLICATIONS

Written Opinion for International Application No. PCT/US2017/048611, dated Dec. 29, 2017.

\* cited by examiner

DEVICE FOR FIXING SPINE

The present invention claims priority to Korean Patent Application No. 10-2017-0002908, filed on Jan. 9, 2017, which is incorporated by reference for all purposes as if fully set forth herein.

BACKGROUND OF THE INVENTION

Field of the Invention

The present invention relates to a hook type patient-specific drill template for spine screw placement, and centralization system for its preparation and use.

Discussion of the Related Art

In 1963, Roy-Camille et al first reported the use of a pedicle screw. Since then, pedicle screw fixation has become a commonly used and minimum invasive procedure. In addition, biomechanical studies have reported superiority of stability and union rate over other posterior fixation.

However, unlike other vertebrae, the thoracic spine has a smaller vertebral body and the use of pedicle screw fixation has been limited due to the risk of soft tissue injury such as peripheral vascular, nerve, muscle, ligament, etc. Therefore, it is difficult to accurately insert the pedicle screw in the site where surgery is needed. When the pedicle screw is inserted inaccurately, injuries to soft tissue, peripheral blood vessels, nerves, muscles, and ligaments often occur. There is a need for accurately insert the pedicle screw.

SUMMARY OF THE INVENTION

In one embodiment, the present invention provides a patient-specific drill template for spine screw placement. The patient-specific drill template includes a hook-shaped main body, and an insertion guiding portion that guides a spine screw to be inserted into a vertebra. The hook-shaped main body includes a tight contact portion and a hook portion, the tight contact portion connecting with insertion guiding portion, the hook portion extending from the tight contact portion, and the hook-shaped main body partially surrounds the vertebra.

In another embodiment, the patient-specific drill template includes a plurality of protrusions, and the plurality of the protrusions are located on an inner surface of the hook portion.

In another embodiment, the patient-specific drill template is made from a titanium alloy, a stainless steel alloy, a bioceramics, a biocompatible acrylic resin, or silicon.

In another embodiment, the patient-specific drill template is made by a 3D printing process.

In another embodiment, the insertion guiding portion has a hollow cylinder shape.

In another embodiment, an inner wall of the insertion guiding portion includes thread.

In another embodiment, the thread of the inner wall of the insertion guiding portion matches the thread of the spine screw.

In one embodiment, the present invention provides a patient-specific drill template kit. The patient-specific drill template includes a patient-specific drill template, and a plurality of spine screws. The patient-specific drill template includes a hook-shaped main body, and an insertion guiding portion that guides the spine screw to be inserted into a vertebra. The hook-shaped main body includes a tight contact portion and a hook portion, the tight contact portion connecting with insertion guiding portion, the hook portion extending from the tight contact portion, and the hook-shaped main body partially surrounds the vertebra.

In another embodiment, the plurality of spine screws are made from a titanium alloy or a stainless steel alloy.

In another embodiment, the patient-specific drill template is made from a titanium alloy, a stainless steel alloy, a bioceramics, a biocompatible acrylic resin, or silicon.

In another embodiment, the patient-specific drill template is made by a 3D printing process.

In another embodiment, the insertion guiding portion has a hollow cylinder shape.

In another embodiment, an inner wall of the insertion guiding portion includes thread, and the spine screws include thread.

In another embodiment, the thread of the inner wall of the insertion guiding portion matches the thread of the spine screws.

In another embodiment, the spine screws include a departure prevention member located at an end thereof.

In one embodiment, the present invention provides a method of preparing a patient-specific drill template for spine screw placement. The method includes preparing a three-dimensional computed tomography of a lumbar or thoracic spine; sending the patient's CT Data to the manufacturing facility through specific network; processing the three-dimensional computed tomography to generate a three-dimensional reconstruction template of the patient-specific drill template; preparing the patient-specific drill template based on the three-dimensional reconstruction template; sterilizing the patient-specific drill template; and packaging the drill template and delivery to each hospital for use.

In another embodiment, the patient-specific drill template includes a hook-shaped main body, and an insertion guiding portion that guides a spine screw to be inserted into a vertebra. The hook-shaped main body includes a tight contact portion and a hook portion, the tight contact portion connecting with insertion guiding portion, the hook portion extending from the tight contact portion, and the hook-shaped main body partially surrounds the vertebra.

In another embodiment, the patient-specific drill template further includes a plurality of protrusions, and the plurality of the protrusions are located on an inner surface of the hook portion.

In another embodiment, the patient-specific drill template is made from a titanium alloy, a stainless steel alloy, a bioceramics, a biocompatible acrylic resin, or silicon.

In another embodiment, the patient-specific drill template is made by a 3D printing process.

In another embodiment, the insertion guiding portion has a hollow cylinder shape.

In another embodiment, an inner wall of the insertion guiding portion includes thread.

In another embodiment, the thread of the inner wall of insertion guiding portion matches the thread of the spine screw.

In another embodiment, the preparing the three-dimensional computed tomography of a lumbar or thoracic spine is conducted in a doctor's office.

In another embodiment, the method further includes after preparing the three-dimensional computed tomography of the lumbar or thoracic spine, forwarding the three-dimensional computed tomography to a manufacturing site.

In another embodiment, the processing the three-dimensional computed tomography is conducted in the manufacturing site.

In another embodiment, preparing the patient-specific drill template based on the three-dimensional reconstruction template is conducted in the manufacturing site.

In another embodiment, the patient-specific drill template is made from a biocompatible acrylic resin.

In another embodiment, the patient-specific drill template is made by a 3D printing process.

In another embodiment, the method further includes after preparing the patient-specific drill template based on the three-dimensional reconstruction template, sending the patient-specific drill template to the doctor's office.

In one embodiment, the present invention provides a method of conducting spine screw placement. The method includes providing a patient-specific drill template, patient-specific drill template having a hook-shaped main body and an insertion guiding portion, the hook-shaped main body including a tight contact portion and a hook portion, the tight contact portion connecting with insertion guiding portion, the hook portion extending from the tight contact portion; placing the patient-specific drill template on a vertebra, the hook-shaped main body partially surrounding the vertebra; providing a spine screw; inserting the spine screw through the patient-specific drill template into the vertebra; and removing the patient-specific drill template.

In another embodiment, the insertion guiding portion has a hollow cylinder shape.

In another embodiment, an inner wall of the insertion guiding portion includes thread.

In another embodiment, the spine screw includes thread.

In another embodiment, the thread of the inner wall of the insertion guiding portion matches the thread of the spine screw.

In another embodiment, the patient-specific drill template is made from a titanium alloy, a stainless steel alloy, a bioceramics, a biocompatible acrylic resin, or silicon.

In another embodiment, the patient-specific drill template is made by a 3D printing process.

In another embodiment, the patient-specific drill template is prepared based a three-dimensional reconstruction template of a lumbar or thoracic spine.

In another embodiment, the patient-specific drill template is prepared in a manufacturing site.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, example of which is illustrated in the accompanying drawings.

Referring to FIGS. 1 to 11, a patient-specific drill template 10 according to an embodiment of the present invention may include a hook-shaped main body 100 and an insertion guiding portion 130. The hook-shaped main body 100 may be placed between spinous process 21 and transverse process 22 of a vertebrae 20 by the operator.

Figure 1:
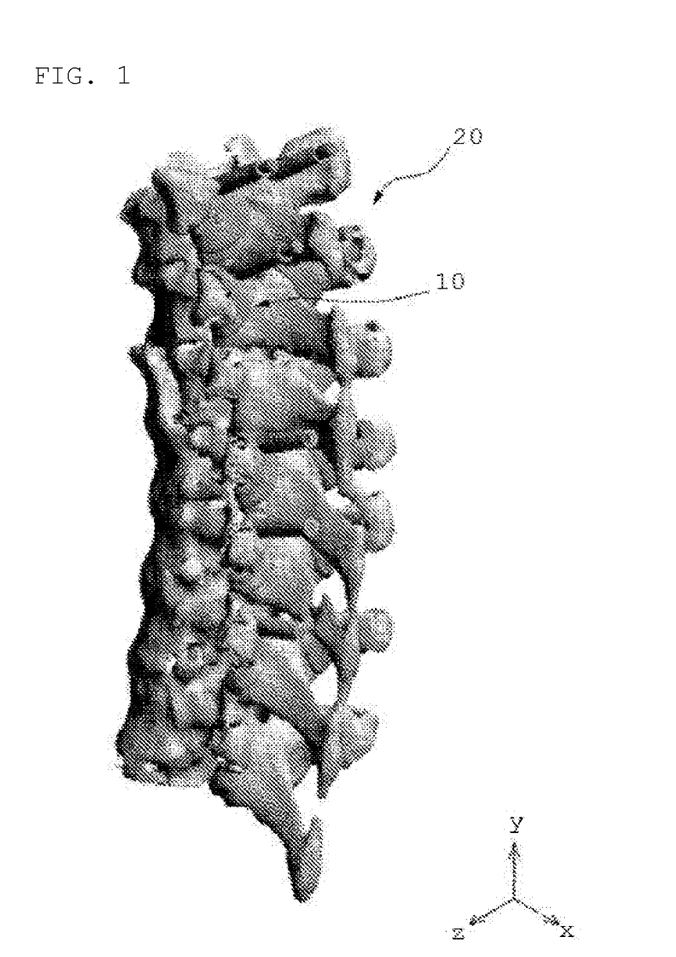
FIG. 1 is a side view of a spine and a patient-specific drill template according to an embodiment of the present invention.
Figure 2:
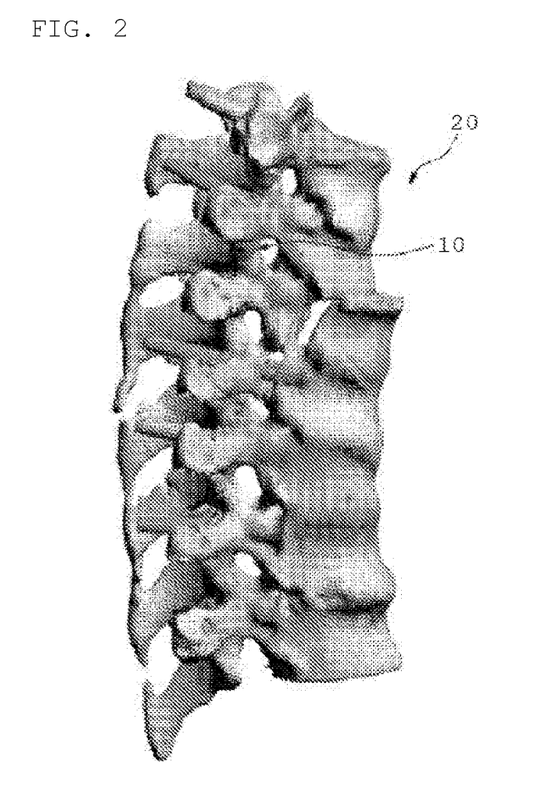
FIG. 2 is another side view of a spine and a patient-specific drill template according to an embodiment of the present invention.
Figure 3:
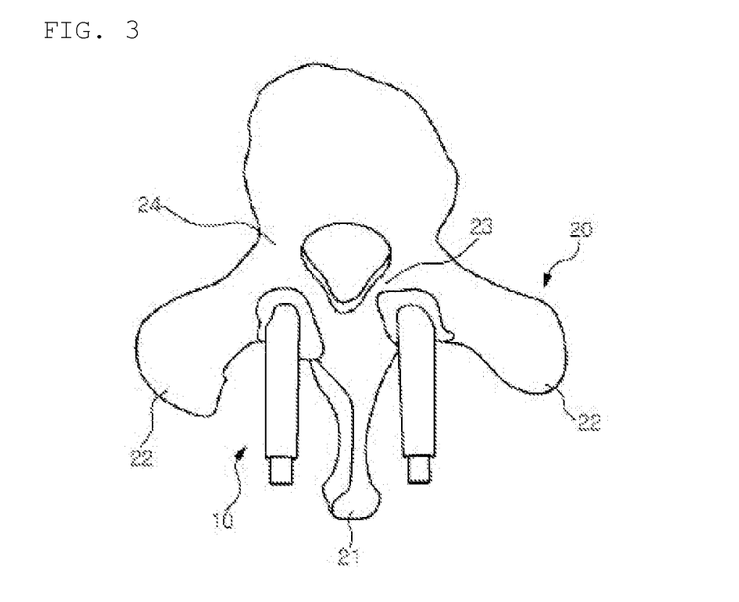
FIG. 3 is a top view of a vertebra and a patient-specific drill template according to an embodiment of the present invention.
Figure 4:
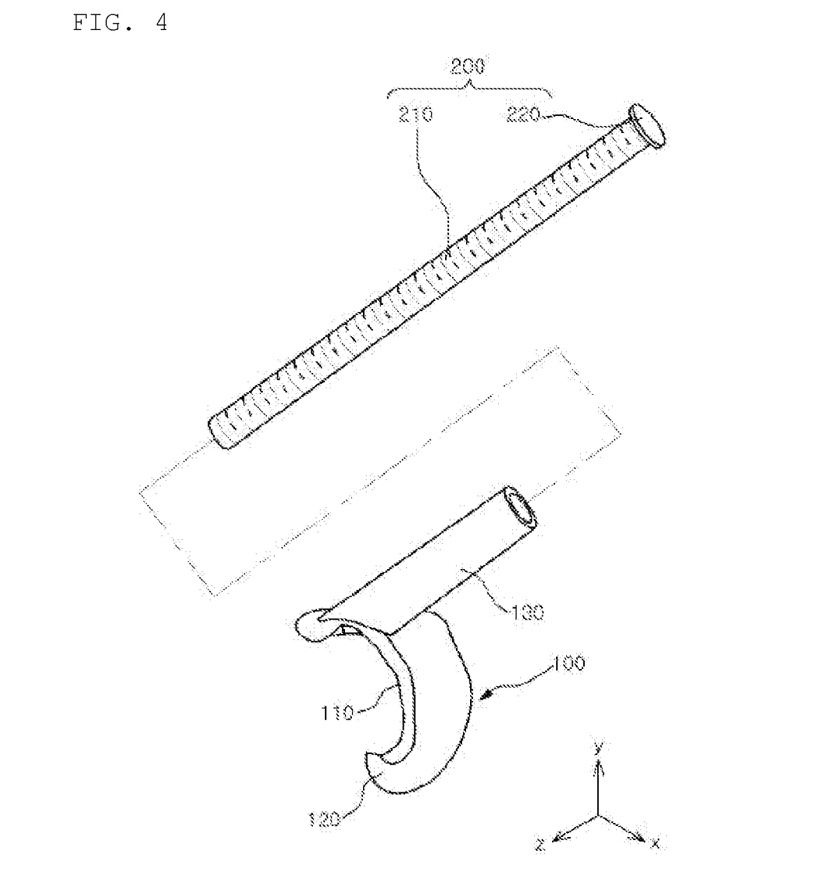
FIG. 4 shows a patient-specific drill template for spine screw placement kit according to an embodiment of the present invention.
Figure 5:
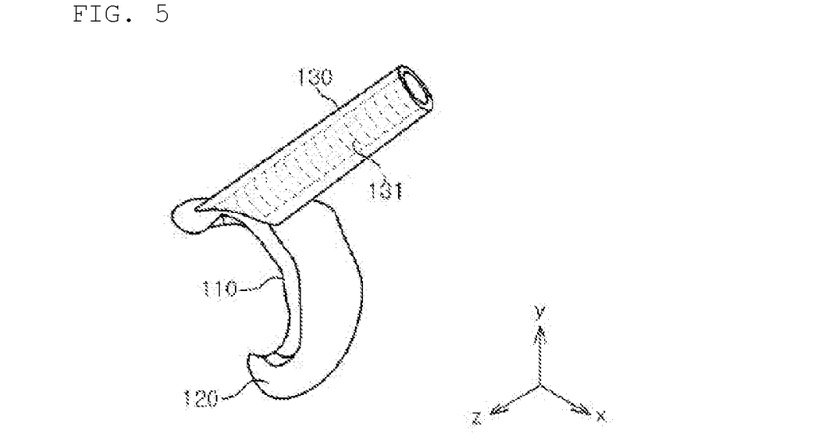
FIG. 5 is a perspective view of a patient-specific drill template according to an embodiment of the present invention.
Figure 6:
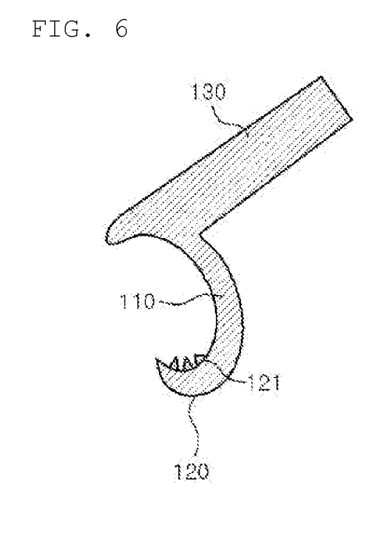
FIG. 6 is a cress-section view of a patient-specific drill template according to an embodiment of the present invention.
Figure 7:
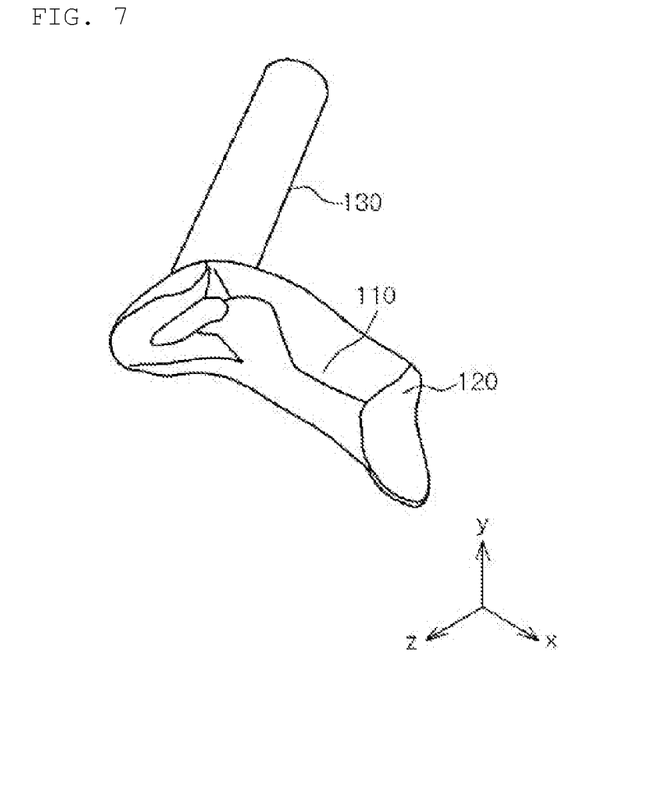
FIG. 7 is a bottom perspective view of a patient-specific drill template according to an embodiment of the present invention.
Figure 8:
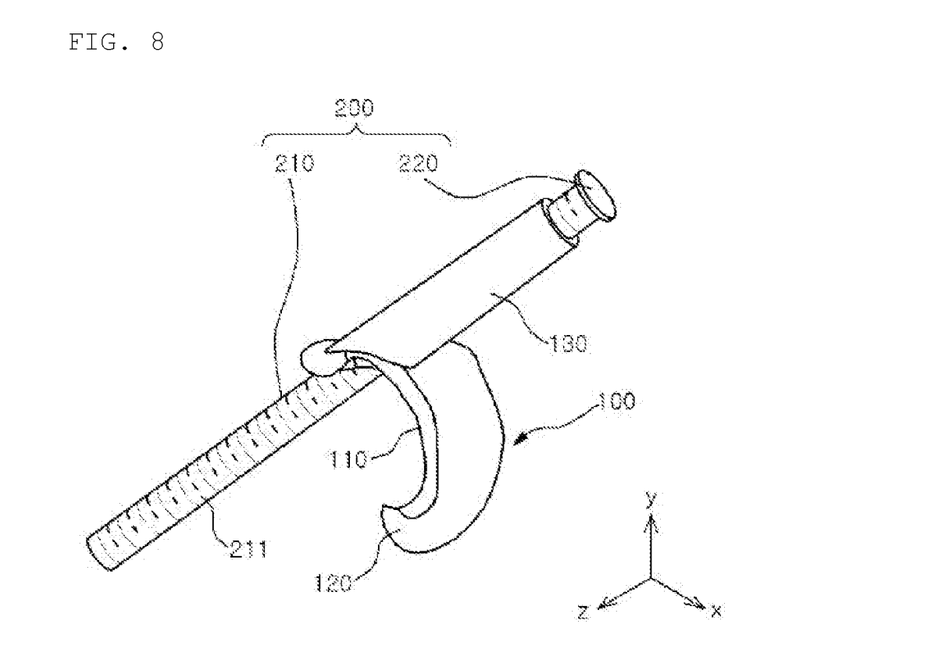
FIG. 8 is a perspective view of a patient-specific drill template for relatively small size vertebra according to an embodiment of the present invention.
Figure 9:
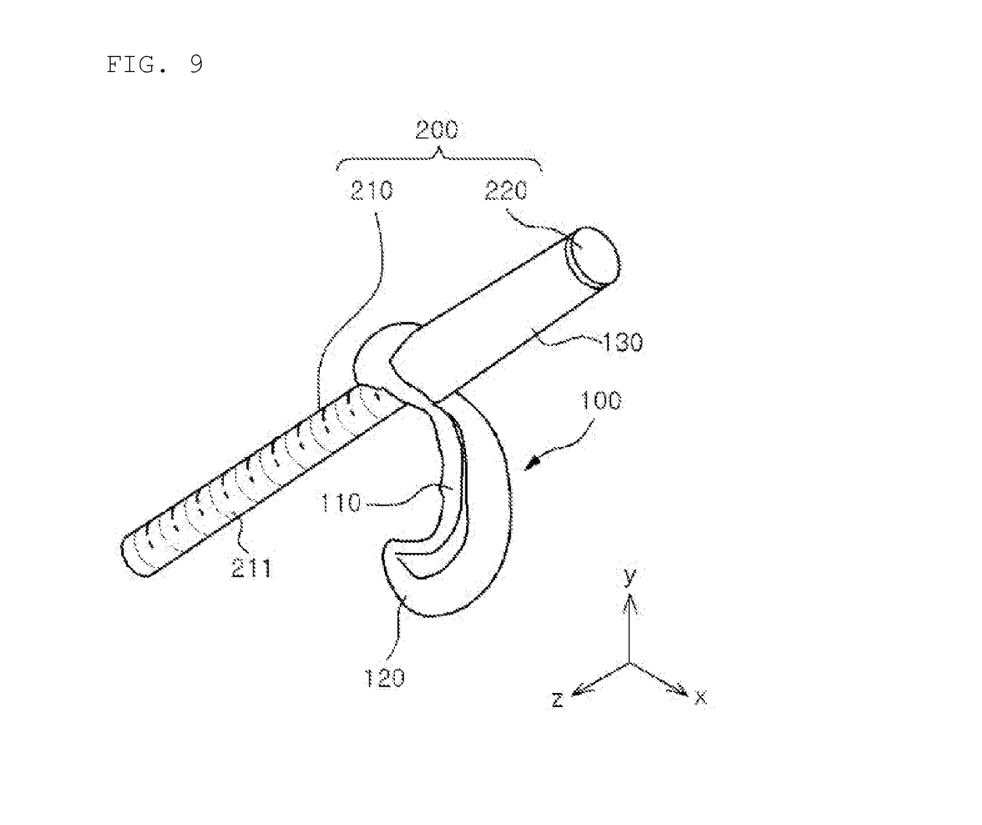
FIG. 9 is a perspective view of a patient-specific drill template for relatively large size vertebra according to an embodiment of the present invention.
Figure 10:
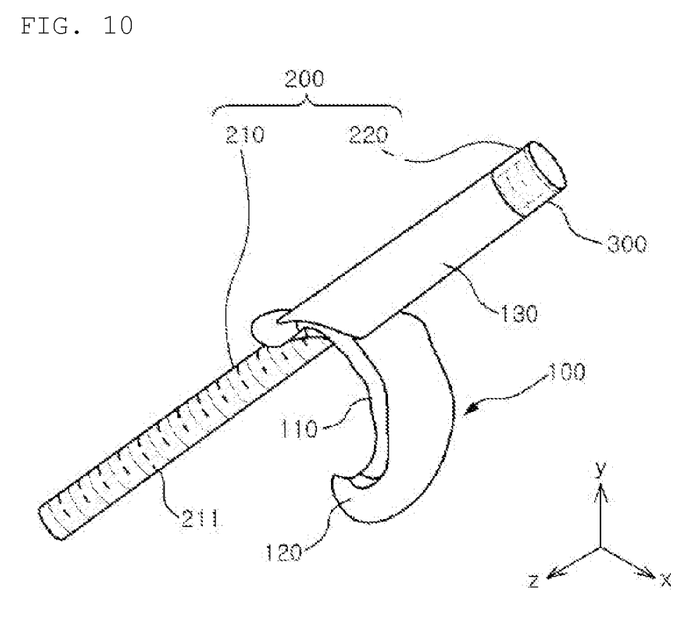
FIG. 10 is a perspective view of a patient-specific drill template with a departure prevention member for relatively small size vertebra according to an embodiment of the present invention.
Figure 11:
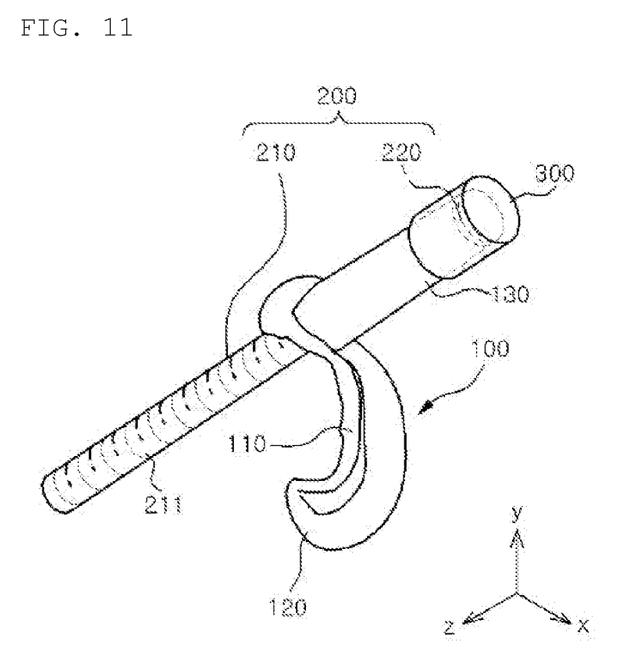
FIG. 11 is a perspective view of a patient-specific drill template with a departure prevention member for relatively large size vertebra according to an embodiment of the present invention.

The hook-shaped main body 100 may include a tight contact portion 110 and a hook portion 120. The tight contact portion 110 can be brought into close contact with the region between the spinous process 21 and the transverse process 22 of the vertebra 20. The tight contact portion 110 can be prepared by a separate 3D modeling operation with respect to the vertebrae 20 of a patient, a 3D printing process, or the like. The tight contact portion 110 is designed to conform to the shape of the region between the spinous process 21 and the transverse process 22 of the vertebra 20. In FIG. 3, lamina 23 and vertebral arch 24 are also shown.

The patient-specific drill template 10 only covers a small region between the spinous process 21 and the transverse process 22 of the vertebra 20, and is smaller than conventional drill template. This can reduce the time and cost required for manufacturing patient-specific drill template 10 and can minimize the damages to the soft tissues, blood vessels, nerves, muscles, ligaments, etc.

Although the patient-specific drill template 10 only covers a small region between the spinous process 21 and the transverse process 22 of the vertebra 20, the patient-specific drill template 10 includes the hook portion 120 that is configured to be hooked around the region between the spinous process 21 and the transverse process 22. The hook portion 120 securely attaches the patient-specific drill template 10 on the vertebra 20.

At least one protrusion 121 may be formed on an inner surface of the hook portion 120. The protrusion 121 increases the contact area between the inner surface of the hook portion 120 and the region between the spinous process 21 and the transverse process 22 of the vertebra 20.

This can further prevent the patient-specific drill template 10 from being detached from the vertebra 20.

The insertion guiding portion 130 can determine the insertion start point and insertion direction of a spine screw 200 and guide the entry of the spine screw 200 so that the spine screw 200 is fastened to the vertebra 20. The spine screw 200 can be, for example, a lumbar or thoracic spine screw.

The insertion guiding portion 130 may be connected to the tight contact portion 110 and may protrude from the outer side of the tight contact portion 110 to the back of the vertebra 20. Here, the back of the vertebrae 20 means the direction toward the back of the operation. The insertion guiding portion may have a hollow cylinder shape. A thread 131 is formed on the inner surface of the insertion guiding portion 130. The spine screw has thread 211 on its outer surface. The thread 131 matches the thread 211 so that the spine screw 200 can be screwed onto the insertion guiding portion 130 and then be inserted to the vertebra 20.

The tight contact portion 110, the insertion guiding portion 130, and the hook portion 120 may be made of a material that has no toxicity and has a similar elasticity and strength to human bone. For example, they may be made of a titanium alloy, a stainless steel alloy, a bioceramics, or a biocompatible acrylic resin. Side effects, such as foreign body reaction and inflammation, can be minimized.

The spine screw 200 can be fastened to the vertebrae 20 by being inserted into the vertebrae 20 in a direction perpendicular to the tight contact portion 110 through the insertion guiding portion 130. The spine screw 200 may include a threaded portion 210 having thread 211 formed on an outer circumferential surface thereof and a head portion 220 connected to an end of the threaded portion 210.

The threaded portion 210 may be inserted into the insertion guiding portion 130 and fastened to the vertebral arch 24 of the vertebra 20. The degree of insertion of the threaded portion 210 of the spine screw 200 inserted into the vertebra 20 may be different for different vertebra on the spine.

The head portion 220 may be in contact with or spaced from the end of the insertion guiding part 120 according to the position of the vertebra 20 to which the thread portion 210 is fastened. For example, when the spine screw 200 is fastened to a relatively small-sized thoracic vertebra (e.g., thoracic vertebra 2, thoracic vertebra 3, etc.), the head portion 220 can be separated from the end of the insertion guiding portion 120.

Alternatively, when the spine screw 200 is fastened to a relatively large sized thoracic spine (e.g., thoracic spine 5, thoracic spine 6, thoracic spine 7). The spine screw 200 can be inserted into the vertebra 20 until the head portion 220 and an end of insertion guiding portion 120 come into contact with each other. Accordingly, the head portion 220 may have a state of being in contact with the end of the insertion guiding portion 120.

In order to prevent the spine screw 200 from being detached from the insertion guiding portion 130, the patient-specific drill template 10 according to one embodiment of the present invention includes a departure prevention member 300.

The departure prevention member 300 may cover an end of the insertion guiding portion 130. For example, when the spine screw 200 is fastened to a vertebra of relatively small size (for example, thoracic vertebra 2, thoracic vertebra 3), the head portion 220 can be fitted to a part of the threaded portion 210 exposed from the end of the insertion guiding portion 130. When the spine screw 200 is fastened to a thoracic vertebra of a relatively large size (for example, thoracic vertebra 5, thoracic vertebra 6, thoracic vertebra 7), the departure prevention member 300 can be fitted to the end of the insertion guiding port 130. The departure prevention member 300 may be a cap member having a cap shape.

Hereinafter, the operation and effects of the patient-specific drill template 10 having the above-described configuration will be described.

First, a patient-specific drill template 10 is fixed in a region between the spinous process 21 and the transverse process 22 to perform an operation of fixing the vertebra 20 of a patient.

To do this, a 3D image of the spine 20 can be acquired by a 3D CT apparatus (LightSpeed VCT, GE Healthcare, Waukesha, Wis., USA). The acquired 3D image can be transferred to a 3D modeling program (MIMICS 17.0, Materialize, Leuven, Belgium) and converted into 3D modeling data.

The shape of the tight contact portion 110 of the hook-shaped main body 100 may be modeled so as to correspond to a region between the spinous process 21 and the transverse process 22. In addition, at least a part of the tight contact portion 110 is bent to extend in the direction of attaching to the region between the spinous process 21 and the transverse process 22 to form the hook portion 120. The insertion guiding portion 130 connected to the outer side of the hook-shaped main body 100 can be further modeled by an operator.

The trajectory, diameter, and length of the spine screw 200 to be inserted into the insertion guiding portion 130 is prepared in a separate 3D modeling program (UG Imageware 12.1, EDS Corp., Dallas, Tex., USA).

Thus, after the 3D modeling operations are completed, the patient-specific drill template 10 can be manufactured by a 3D printer (Stratasys Co., Eden Prairie, Minn., USA).

After the patient-specific drill template 10 is obtained, the surgery for fully stabilizing the vertebra 20 can be started. The surgical site of the patient is exposed through a rear incision and the hook-shaped main body 100 is fixed to the area between the spinous process 21 and the transverse process 22 through the exposed site.

The soft tissues around the region between the spinous process 21 and the transverse process 22 are removed. Then, a pilot hole is formed by using a drill at an insertion point in the lamina 23 of the vertebra 20.

When the spine screw 200 is inserted into the pilot hole, the screw member 200 is guided by the insertion guiding portion 120. The departure prevention member 300 is engaged with the end of the insertion guiding portion 130 in which the spine screw 200 is inserted so that the spine screw 200 is prevented from being detached from the insertion guiding portion 130.

The spine screw 200 includes a head portion 220. In a relatively small size thoracic vertebra (e.g., a thoracic vertebra 2, a thoracic vertebra 3), spine screw 200 can be fastened only until it completely abuts against the end of the insertion guiding portion 130.

In contrast, for a relatively large size vertebra (e.g., thoracic spine 5, thoracic spine 6, thoracic spine 7), the spine screw 200 can be fastened until it completely abuts the end of the insertion guiding portion 130. Accordingly, it is possible to fix the vertebra 20 by applying a fastening force of an appropriate size according to the position and size of the vertebra 20.

Finally, vertebral fusion surgery is completed by resealing the incision site.

The inventors of the present invention performed the operation using the patient-specific drill template 10 by the above-described method, and after the operation was completed, the position of the spine screw 200 was determined through thoracic computed tomography. As a result, it was confirmed that all of the spine screws 200 have a deviation of 2 mm or less.

The patient-specific drill template 10 has a structure in which the hook-shaped main body 100 does not cover the spinous process 21 and the transverse process 22. The removal of the surrounding soft tissues can be reduced compared to the conventional method. Accordingly, complication due to soft tissue removal can be reduced compared with the conventional method.

In addition, since the tight contact portion 110 is designed to conform to the shape of the area between the spinous process 21 and the transverse process 22, it is possible to provide patient specific drill template.

In addition, since the spine screw 200 is fastened to the vertebra 20 while being inserted by the insertion guiding portion 130, the insertion and fastening of the spine screw 200 does not completely depend on the operator's anatomical knowledge. This can improve the accuracy of the insertion of the spine screw 200.

In addition, the cost of manufacturing the patient-specific drill template 10 can be low (about 10 dollars). Thus, the manufacturing cost of the patient-specific drill template 10 can be reduced compared to the conventional method.

In addition, as the end of the insertion guiding portion 130 is covered by the departure prevention member 300, the spine screw 200 is prevented from being detached from the insertion guiding portion 130, and the spine screw 200 can be prevented from being changed in advance. Therefore, the patient-specific drill template 10 can be firmly fixed in the region between the spinous process 21 and the transverse process 22, and even if an external force is applied to the fixed position of the patient-specific drill template 10.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A patient-specific drill template for spine screw placement, comprising:
    a hook-shaped main body; and
    an insertion guiding portion extending from a surface of the hook-shaped main body in a longitudinal direction to guide a spine screw to be inserted into a vertebra,
    wherein the hook-shaped main body includes a tight contact portion and a hook portion, the tight contact portion connecting with the insertion guiding portion, and the hook portion bending and extending in an arc shape from at least a portion of an edge of the tight contact portion,
    wherein the hook-shaped main body is configured to partially surround the vertebra, and
    wherein the insertion guiding portion includes a through-hole formed in the longitudinal direction of the insertion guiding portion.

2. The patient-specific drill template of claim 1, further comprising a plurality of protrusions located on an inner surface of the hook portion.

3. The patient-specific drill template of claim 1, wherein the patient-specific drill template is made from a titanium alloy, a stainless steel alloy, a bioceramics, a biocompatible acrylic resin, or silicon.

4. The patient-specific drill template of claim 1, wherein patient-specific drill template is made by a 3D printing process.

5. The patient-specific drill template of claim 1, wherein the insertion guiding portion has a hollow cylinder shape.

6. A patient-specific drill template kit, comprising:
    a patient-specific drill template; and
    a spine screw,
    wherein the patient-specific drill template comprises:
    a hook-shaped main body; and
    an insertion guiding portion extending from a surface of the hook-shaped main body in a longitudinal direction to guide the spine screw to be inserted into a vertebra,
    wherein the hook-shaped main body includes a tight contact portion and a hook portion, the tight contact portion connecting with the insertion guiding portion, and the hook portion bending and extending in an arc shape from at least a portion of an edge of the tight contact portion,
    wherein the hook-shaped main body is configured to partially surround the vertebra, and
    wherein the insertion guiding portion includes a through-hole formed in the longitudinal direction of the insertion guiding portion.

7. The patient-specific drill template kit of claim 6, wherein the spine screw is made from a titanium alloy or a stainless steel alloy.

8. The patient-specific drill template kit of claim 6, wherein the patient-specific drill template is made from a titanium alloy, a stainless steel alloy, a bioceramics, a biocompatible acrylic resin, or silicon.

9. The patient-specific drill template kit of claim 6, wherein the patient-specific drill template is made by a 3D printing process.

10. The patient-specific drill template kit of claim 6, wherein the insertion guiding portion has a hollow cylinder shape.

11. The patient-specific drill template kit of claim 6, wherein the spine screw includes a departure prevention member located at an end thereof.

12. A method of preparing a patient-specific drill template for spine screw placement, the method comprising:
    preparing a three-dimensional computed tomography of a lumbar or thoracic spine;
    processing the three-dimensional computed tomography to generate a three-dimensional reconstruction template of the patient-specific drill template;
    preparing the patient-specific drill template based on a three-dimensional reconstruction template; and
    sterilizing the patient-specific drill template,
    wherein the patient-specific drill template comprises:
    a hook-shaped main body; and
    an insertion guiding portion extending from a surface of the hook-shaped main body in a longitudinal direction to guide a spine screw to be inserted into a vertebra,
    wherein the hook-shaped main body includes a tight contact portion and a hook portion, the tight contact portion connecting with the insertion guiding portion, and the hook portion bending and extending in an arc shape from at least a portion of an edge of the tight contact portion,
    wherein the hook-shaped main body is configured to partially surround the vertebra, and
    wherein the insertion guiding portion includes a through-hole formed in the longitudinal direction of the insertion guiding portion.

13. The method of claim 12, wherein the patient-specific drill template further comprises a plurality of protrusions located on an inner surface of the hook portion.

14. The method of claim 12, wherein the patient-specific drill template is made from a titanium alloy, a stainless steel alloy, a bioceramics, a biocompatible acrylic resin, or silicon.

15. The method of claim 12, wherein the patient-specific drill template is made by a 3D printing process.

16. The method of claim 12, wherein the insertion guiding portion has a hollow cylinder shape.

17. The method of claim 12, wherein the preparing of the three-dimensional computed tomography of the lumbar or thoracic spine is conducted in a doctor's office.

18. The method of claim 17, further comprising:
after preparing the three-dimensional computed tomography of the lumbar or thoracic spine, forwarding the three-dimensional computed tomography to a manufacturing site.

19. The method of claim 18, wherein the processing of the three-dimensional computed tomography is conducted in the manufacturing site.

20. The method of claim 19, wherein the preparing of the patient-specific drill template based on the three-dimensional reconstruction template is conducted in the manufacturing site.

21. The method of claim 20, wherein the patient-specific drill template is made from a biocompatible acrylic resin.

22. The method of claim 21, wherein the patient-specific drill template is made by a 3D printing process.

23. The method of claim 18, further comprising:
after preparing the patient-specific drill template based on the three-dimensional reconstruction template, sending the patient-specific drill template to the doctor's office.

24. A method of conducting spine screw placement, the method comprising:
providing a patient-specific drill template having a hook-shaped main body and an insertion guiding portion extending from a surface of the hook-shaped main body in a longitudinal direction, the hook-shaped main body including a tight contact portion and a hook portion, the tight contact portion connecting with the insertion guiding portion, and the hook portion bending and extending in an arc shape from at least a portion of an edge of the tight contact portion;
placing the patient-specific drill template on a vertebra for the hook-shaped main body to partially surround the vertebra;
providing a spine screw;
inserting the spine screw through the patient-specific drill template into the vertebra; and
removing the patient-specific drill template,
wherein the insertion guiding portion includes a through-hole formed in the longitudinal direction of the insertion guiding portion.

25. The method of claim 24, wherein the insertion guiding portion has a hollow cylinder shape.

26. The method of claim 24, wherein the patient-specific drill template is made from a titanium alloy, a stainless steel alloy, a bioceramics, a biocompatible acrylic resin, or silicon.

27. The method of claim 24, wherein the patient-specific drill template is made by a 3D printing process.

28. The method of claim 24, wherein the patient-specific drill template is prepared based a three-dimensional reconstruction template of a lumbar or thoracic spine.

29. The method of claim 28, wherein the patient-specific drill template is prepared in a manufacturing site.

* * * * *

UNITED STATES PATENT AND TRADEMARK OFFICE
CERTIFICATE OF CORRECTION

| | |
|---|---|
| PATENT NO. | : 11,246,608 B2 |
| APPLICATION NO. | : 16/476405 |
| DATED | : February 15, 2022 |
| INVENTOR(S) | : Won |

Page 1 of 1

It is certified that error appears in the above-identified patent and that said Letters Patent is hereby corrected as shown below:

On the Title Page

Item (71) should read:
(71) Applicant: Yougun Won, Daejeon (KR);
BIOCOEN CO., LTD., Pyeongtaek-si, Gyeonggi-do (KR)

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*